(12) United States Patent
Sooudi et al.

(10) Patent No.: US 11,010,758 B2
(45) Date of Patent: May 18, 2021

(54) DIGITAL WALLET NOTIFICATION SYSTEMS AND METHODS

(71) Applicant: Aptus Health, Inc., Reading, MA (US)

(72) Inventors: Hossain Sooudi, Atlanta, GA (US); Joe Jackson, Canton, GA (US); Or Maoz, Dunwoody, GA (US)

(73) Assignee: Aptus Health, Inc., Reading, MA (US)

( * ) Notice: Subject to any disclaimer, the term of this patent is extended or adjusted under 35 U.S.C. 154(b) by 599 days.

(21) Appl. No.: 15/483,364

(22) Filed: Apr. 10, 2017

(65) Prior Publication Data
US 2018/0293574 A1 Oct. 11, 2018

(51) Int. Cl.
| | |
|---|---|
| *G06Q 20/36* | (2012.01) |
| *G06Q 50/22* | (2018.01) |
| *G06Q 20/32* | (2012.01) |
| *G06Q 20/38* | (2012.01) |
| *G06Q 20/40* | (2012.01) |

(52) U.S. Cl.
CPC ..... *G06Q 20/3672* (2013.01); *G06Q 20/3224* (2013.01); *G06Q 20/385* (2013.01); *G06Q 20/387* (2013.01); *G06Q 20/405* (2013.01); *G06Q 50/22* (2013.01)

(58) Field of Classification Search
CPC .. G06Q 20/36; G06Q 20/3674; G06Q 20/322; G06Q 20/385; G06Q 20/405
See application file for complete search history.

(56) References Cited

U.S. PATENT DOCUMENTS

| | | | |
|---|---|---|---|
| 4,766,542 | A | 8/1988 | Pilarczyk |
| 5,832,449 | A | 11/1998 | Cunningham |
| 5,970,462 | A | 10/1999 | Reichert |
| 6,055,507 | A | 4/2000 | Cunningham |
| 6,859,780 | B1 | 2/2005 | Cunningham |
| 7,426,476 | B2 | 9/2008 | Munoz et al. |

(Continued)

FOREIGN PATENT DOCUMENTS

WO 2009010868 A2 1/2009

OTHER PUBLICATIONS

U.S. Appl. No. 15/483,481, filed Apr. 10, 2017 Final Office Action dated Jan. 2, 2020.

(Continued)

*Primary Examiner* — Jonathan Durant
(74) *Attorney, Agent, or Firm* — Rutan & Tucker, LLP

(57) ABSTRACT

A method includes receiving by a processor a prescription drug claim transaction data from a claims processor over a data communications network, analyzing the prescription drug claim transaction data by the processor, identifying by the processor from the prescription drug claim transaction data an entity selected from the group consisting of: prescribing doctor and dispensing pharmacy, determining by the processor a location of the entity, and generating by the processor a token for the digital wallet of the user device, the token includes rules for displaying a message in the user device when the user device passes to within a threshold distance of the location of the entity as detected by a location sensor of the user device. The rules cause display of the message in the user device when the user device passes to within a threshold distance of the location of the entity as detected by a location sensor of the user device.

9 Claims, 4 Drawing Sheets

(56) References Cited

U.S. PATENT DOCUMENTS

| | | |
|---|---|---|
| 7,729,927 B2 | 6/2010 | Cunningham |
| 7,827,041 B2 | 11/2010 | Roberts et al. |
| 7,848,934 B2 | 12/2010 | Kobylevsky et al. |
| 7,925,531 B1 | 4/2011 | Cunningham et al. |
| 7,996,243 B1 | 8/2011 | Ali et al. |
| 7,996,260 B1 | 8/2011 | Cunningham et al. |
| 8,055,542 B1 | 11/2011 | Cunningham et al. |
| 8,407,095 B2 | 3/2013 | Cunningham et al. |
| 8,589,184 B2 | 11/2013 | Cunningham et al. |
| 8,639,523 B1 | 1/2014 | Pinsonneault |
| 9,355,391 B2 | 5/2016 | von Beheren et al. |
| 10,210,311 B1 | 2/2019 | Taneja |
| 2002/0017904 A1 | 2/2002 | Ott et al. |
| 2002/0065713 A1 | 5/2002 | Awada et al. |
| 2002/0179704 A1 | 12/2002 | Deaton |
| 2003/0154106 A1 | 8/2003 | Marks |
| 2005/0033610 A1 | 2/2005 | Cunningham |
| 2006/0229915 A1 | 10/2006 | Kosinski et al. |
| 2007/0143138 A1 | 6/2007 | Ross et al. |
| 2007/0162309 A1 | 7/2007 | Denny |
| 2007/0164096 A1 | 7/2007 | Banfield et al. |
| 2007/0174092 A1 | 7/2007 | Lara et al. |
| 2007/0191985 A1 | 8/2007 | Bain |
| 2008/0082351 A1* | 4/2008 | Kelley-Hrabe ........ G06Q 50/22 705/2 |
| 2008/0091475 A1 | 4/2008 | Sottile |
| 2008/0103817 A1 | 5/2008 | Bohlke |
| 2008/0147546 A1 | 6/2008 | Weichselbaumer et al. |
| 2008/0154635 A1 | 6/2008 | Babyak et al. |
| 2009/0048712 A1 | 2/2009 | Rosenblum |
| 2009/0164376 A1 | 6/2009 | Guthrie |
| 2010/0082373 A1 | 4/2010 | Fiedotin et al. |
| 2011/0282690 A1 | 11/2011 | Patel et al. |
| 2011/0301973 A1 | 12/2011 | Cunningham et al. |
| 2011/0320345 A1 | 12/2011 | Taveau et al. |
| 2012/0078900 A1 | 3/2012 | Cunningham et al. |
| 2012/0089443 A1 | 4/2012 | Cunningham et al. |
| 2012/0158430 A1 | 6/2012 | MacDonald |
| 2012/0239417 A1* | 9/2012 | Pourfallah ............ G06Q 50/22 705/2 |
| 2012/0245956 A1 | 9/2012 | Damji |
| 2012/0259653 A1 | 10/2012 | Cunningham et al. |
| 2013/0041675 A1 | 2/2013 | Cunningham et al. |
| 2013/0144635 A1 | 6/2013 | Bertha et al. |
| 2013/0218595 A1 | 8/2013 | Burkett |
| 2013/0246087 A1 | 9/2013 | Cunningham et al. |
| 2013/0246092 A1 | 9/2013 | Cunningham et al. |
| 2013/0325569 A1 | 12/2013 | Holmes et al. |
| 2014/0074494 A1 | 3/2014 | Cunningham et al. |
| 2014/0081668 A1 | 3/2014 | Cunningham et al. |
| 2015/0032626 A1* | 1/2015 | Dill ..................... G06Q 20/385 705/44 |
| 2015/0127367 A1 | 5/2015 | Sexton et al. |
| 2015/0205936 A1 | 7/2015 | Ford et al. |
| 2016/0055513 A1 | 2/2016 | Kuhn et al. |
| 2016/0140593 A1 | 5/2016 | Smeeding et al. |
| 2016/0148197 A1* | 5/2016 | Dimmick ........... G06Q 20/3674 705/67 |
| 2016/0180332 A1 | 6/2016 | Wilczynski |
| 2018/0293358 A1 | 10/2018 | Sooudi et al. |

OTHER PUBLICATIONS

U.S. Appl. No. 15/483,481, filed Apr. 10, 2017 Non-Final Office Action dated May 3, 2019.

* cited by examiner

DIGITAL WALLET NOTIFICATION SYSTEMS AND METHODS

TECHNICAL FIELD

The present disclosure relates generally to digital wallets, and more particularly relates to location messaging based on rules of a token stored on a digital wallet.

BACKGROUND

Digital wallets are often used to conduct commerce. The digital wallets may retain or connect to servers that maintain payment information for transacting purchases. Digital wallets may also retain or connect to servers that maintain coupons, ads, information, and other tokens that are available to the digital wallet.

Cell phones and other mobile devices may include a digital wallet. The digital wallet presents payment information at point of sale to complete a purchase. Coupons, ads, information, and other tokens saved to the digital wallet may be enabled for availability in effecting the sale.

Cell phones and other mobile devices may include global positioning system (GPS) units or other location based detectors. Those detectors locate the devices by longitude and latitude coordinates.

It would be a significant improvement in the art and technology to provide location-based messaging in devices through digital wallet tokens.

SUMMARY

An embodiment of the invention is a system for display of a message in a user device having a digital wallet and a location sensor. A data communications network is communicatively connected to a claims processor and the user device. The system includes a processor, a network interface communicatively connected to the processor and the data communications network, a memory communicatively connected to the processor, the memory includes instructions for causing the processor to receive over the data communications network from the claims processor a set of prescription drug claims data associated with the user device, analyze the prescription drug claims data, identify an entity of the prescription drug claims data selected from the group consisting of: prescribing doctor and dispensing pharmacy, determine a location of the entity, and generate a token for the digital wallet of the user device, the token includes rules for displaying a message in the user device when the user device passes to within a threshold distance of the location of the entity as per the location sensor.

Another embodiment of the invention is a method including receiving by a processor a prescription drug claim transaction data from a claims processor over a data communications network, analyzing the prescription drug claim transaction data by the processor, identifying by the processor from the prescription drug claim transaction data an entity selected from the group consisting of: prescribing doctor and dispensing pharmacy, determining by the processor a location of the entity, and generating by the processor a token for the digital wallet of the user device, the token includes rules for displaying a message in the user device when the user device passes to within a threshold distance of the location of the entity as detected by a location sensor of the user device.

Yet another embodiment of the invention is a system including a program processor, a claims processor communicatively connected to the program processor, a pharmacy gateway communicatively connected to the claims processor, and a user device communicatively connected to the program processor and the pharmacy gateway, the user device includes a digital wallet having a prescription drug co-pay card token and a location sensor. The user device redeems the prescription drug co-pay card token on purchase of a prescription drug from the pharmacy gateway, the pharmacy gateway enters prescription drug claims data for the purchase of the prescription drug, the prescription drug claims data is received by the claims processor from the pharmacy gateway and the claims processor adjudicates the prescription drug claims data for benefit coverage, and the program processor obtains the prescription drug claims data from the claims processor, analyzes the prescription drug claims data, identifies an entity selected from the group consisting of: prescribing doctor and dispensing pharmacy, determines a location of the entity, and generates an updated token for the digital wallet of the user device, the updated token includes rules for display of a message in the user device if and when the user device passes to within a threshold distance of the location of the entity as per the location sensor.

Another embodiment of the invention is a method including presenting a prescription drug co-pay card token by a digital wallet of a user device to a pharmacy gateway at point of purchase of a prescription drug associated with the co-pay card token, the user device includes a location sensor, receiving prescription drug claims data by the pharmacy gateway related to the purchase of the prescription drug, communicating the prescription drug claims data by the pharmacy gateway to a claims processor communicatively connected to the pharmacy gateway, obtaining the prescription drug claims data from the claims processor by a program processor communicatively connected to the claims processor, analyzing the prescription drug claims data by the program processor, identifying by the program processor a prescribing doctor or dispensing pharmacy associated with the prescription drug claims data, determining by the program processor a location of the prescribing doctor or dispensing pharmacy, and generating an updated token for the digital wallet of the user device, the updated token includes rules for display of a message in the user device when the user device passes to within a threshold distance of the location as per the location sensor.

BRIEF DESCRIPTION OF THE DRAWINGS

The present invention is illustrated by way of example and not limitation in the accompanying figures, in which like references indicate similar elements, and in which.

DETAILED DESCRIPTION

In an example embodiment, a user of a digital wallet on a cell phone or other device downloads a token, such as a co-pay card for a prescription drug transaction. The token is available from a website, click on an email, through an app downloaded to the device, or other source. The user redeems or uses the token by completing a purchase of the prescription drug from a pharmacy gateway. Upon the purchase, the prescription drug claims data for the purchase is communicated by the pharmacy gateway to a claims processor. A program processor may obtain the prescription drug claims data from the claims processor and analyze the data. From the prescription drug claims data, identities of the prescribing physician and the pharmacy of the purchase are determined by the program processor. From those identities, locations of the prescribing physician and pharmacy of the purchase may be determined by the program processor. The program processor may translate the locations to longitude and latitude coordinates. The program processor may deliver an updated token to the digital wallet of the device. The updated token may include rules for causing the device of the digital wallet to display a coupon, ad, or other information if and when the device of the digital wallet is within a range of the physician or pharmacy location as detected by a location detector of the device.

Figure 1:
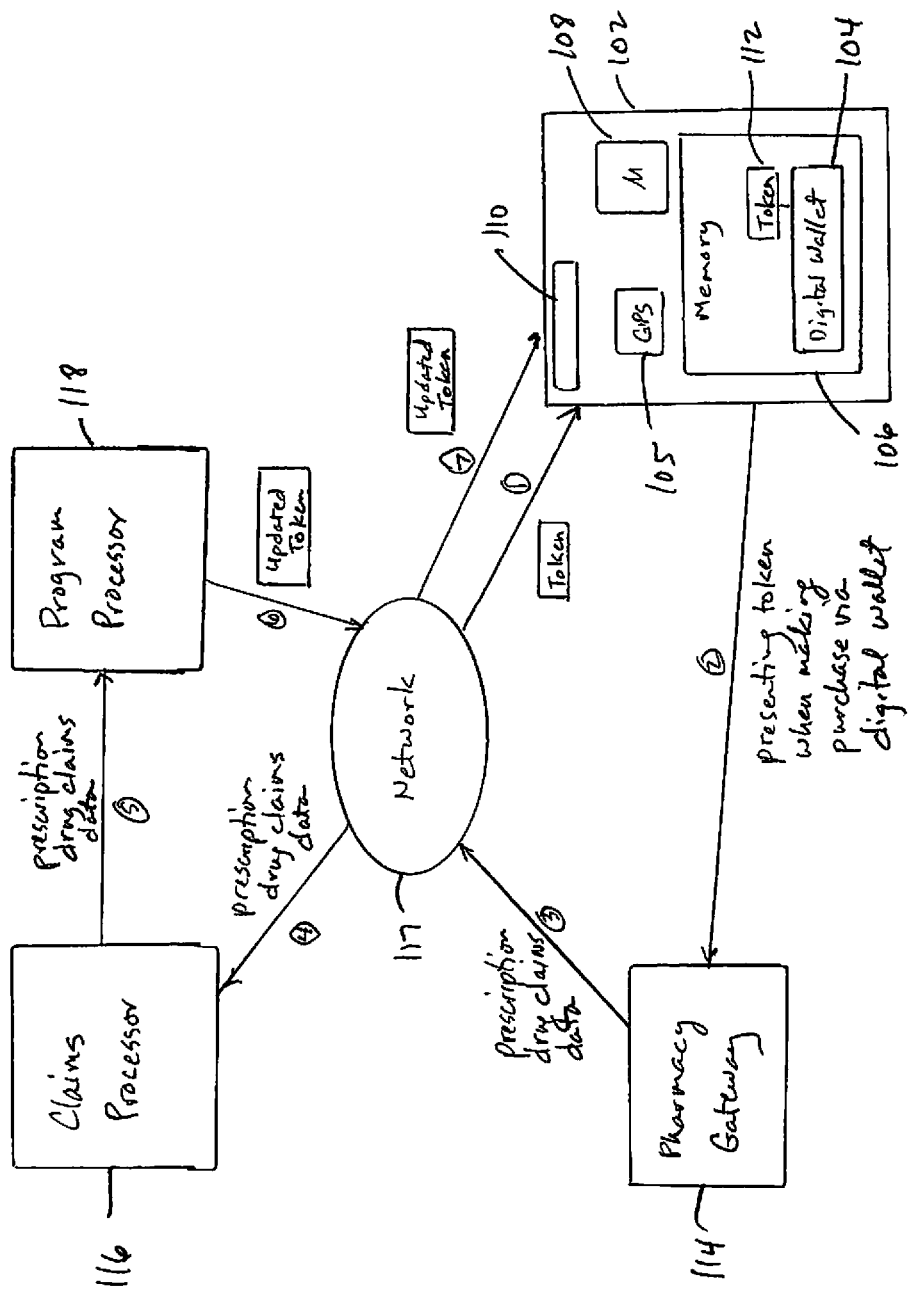
FIG. 1 illustrates a system for location-based messaging via a digital wallet token of a user device, according to certain embodiments of the invention.

Referring to FIG. 1, a system 100 includes a user device 102 having a digital wallet 104. The digital wallet 104 is, for example, a digital wallet software program stored in memory 106 of the user device 102, electronic circuits of the user device 102 operating as the digital wallet, or combinations. The digital wallet 104 is operated by a processor 108 of the user device 102. The user device 102 includes a communication interface 110 for communicating over a network 110. The user device 102 also includes a location sensor 105, such as a global positioning system (GPS) unit, for locating the user device 102.

The digital wallet 104 collects a token 112. The token 112 is, for example, a co-pay card for purchase of a prescription drug. The token 112 is collected by the digital wallet 104 via download from a website, click on email directing to the token 112, an app downloaded to the user device 102, or otherwise.

The token 112 is redeemable or useable in connection with a purchase made via the digital wallet 104. For example, the digital wallet 104 presents the token 112 at a point of sale of a pharmacy or other retailer, such as to obtain a discount or other award in connection with a purchase. In certain embodiments described in detail, the token 112 is a co-pay card for discount on purchase of a prescription drug at a point of sale of a pharmacy gateway 114.

At the pharmacy gateway 114, prescription drug claims data is entered or received when fill of the prescription drug of the token 112 is requested from the pharmacy. The prescription drug claims data includes details of a transaction for purchase of a prescription drug, including identity of the prescribing doctor and identity of the dispensing pharmacy. The pharmacy gateway 114 may be one or more computer or point of sale device that captures entered prescription drug claims data. The pharmacy gateway 114 includes a communication interface 115 for communicating with a claims processor 116 over a network.

The pharmacy gateway 114 communicates the prescription drug claims data to the claims processor 116. The claims processor 116 adjudicates the prescription drug purchase transaction for the prescription drug claims data, to determine any coverage benefit associated with the prescription drug. The claims processor 116 may be one or more computer or processing device, and may include or communicatively connect to one or more database of benefits coverage information.

A program processor 118 is communicatively connected to the claims processor 116 for obtaining the prescription drug claims data and analyzing it. The program processor 118 may receive the prescription drug claims data via an application programming interface (API) of the claims processor 116 for such purpose, via a secure file transfer protocol (SFTP) server for such purpose, or other interface. The program processor 118 obtains and analyzes the prescription drug claims data and determines identity of the prescribing doctor and/or identity of the dispensing pharmacy. Based on those identities, the program processor 118 determines a location for the prescribing doctor and/or a location for the dispensing pharmacy. The program processor 118 may be one or more computer or processing device capable of communicating with the claims processor 116 to obtain prescription drug claims data and analyze the data.

The program processor 118, either itself or through communicative connection to other devices, translates the locations of the prescribing doctor and/or the dispensing pharmacy to longitude and latitude coordinates. Based on the longitude and latitude coordinates, the program processor 118 (or other device communicatively connected to the program processor 118) generates a token update 120 for the digital wallet 104 of the user device 102. The token update 120 includes rules for display of a message on the user device 102 if and when the user device 102 moves to within a threshold distance of the longitude and latitude coordinates as dictated by the location of the user device 102 per the location sensor 105.

The token update 120 is delivered to the digital wallet 104 of the user device 102. The token update 120 may be pushed to the digital wallet 104, downloaded by the digital wallet 104 from a website or URL link, via click on an email directed to the token update 120, via an app of the user device 102, or otherwise. If and when the user device 102 moves to within a threshold distance of the longitude and latitude coordinates, the token update 120, via rules, displays in the user device a relevant message.

Figure 2:
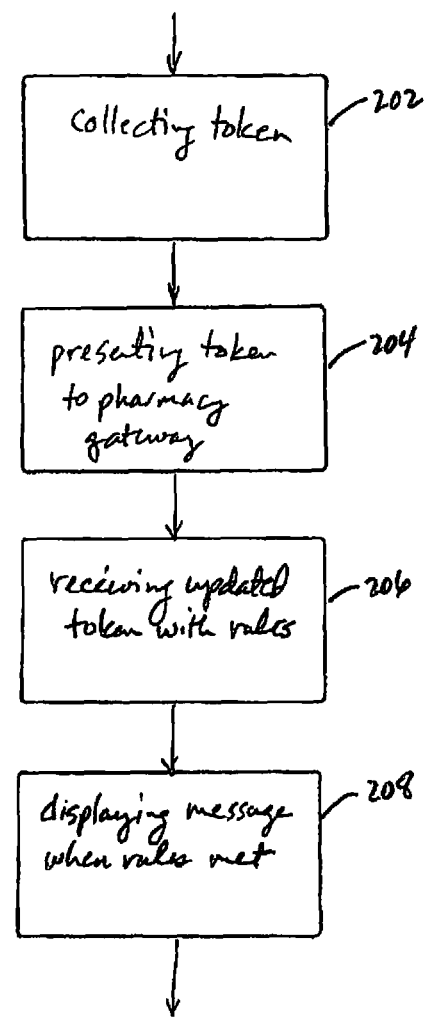
FIG. 2 illustrates a method of operations of a user device having a digital wallet and tokens, according to certain embodiments of the invention.

Referring to FIG. 2, a method 200 of operations of a user device having a digital wallet includes collecting 202 a token to the digital wallet. The token is a co-pay card for a prescription drug. The digital wallet presents 204 the token to a pharmacy gateway at point of purchase of the prescription drug.

The pharmacy gateway captures prescription drug claims data in connection with the purchase. The prescription drug claims data is communicated to a claims processor. The claims processor adjudicates the prescription drug transaction, to determine any coverage benefit applicable to the transaction. The purchase of the prescription drug accounts for the coverage benefit and any co-pay amount that may apply.

A program processor obtains the prescription drug claims data from the claims processor. The program processor analyzes the prescription drug claims data to identify the prescribing doctor and/or the pharmacy for the transaction. The program processor determines a location of the prescribing doctor and/or the pharmacy for the transaction.

The program processor generates an updated token with rules for the location. The updated token is delivered 206 to the digital wallet.

If and when the digital wallet passes to within a threshold distance of the location, as set for the updated token by the rules for the location, a message is displayed 208 in the user device of the digital wallet.

Figure 3:
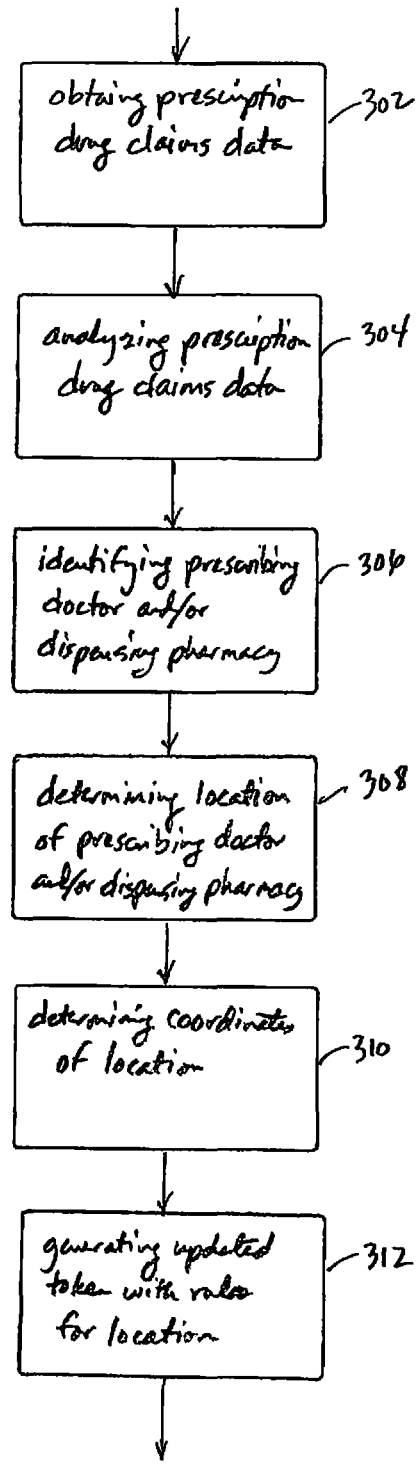
FIG. 3 illustrates a method of operations of a program processor for generating a token with rules for display of messaging based on location, according to certain embodiments of the invention.

Referring to FIG. 3, a method 300 of operations of a program processor includes obtaining 302 prescription drug claims data from a claims processor. The prescription drug claims data is analyzed 304 by the program processor. The program processor identifies 306 a prescribing doctor and/or pharmacy associated with the prescription drug of the prescription drug claims data.

The program processor determines 308 a location of the prescribing doctor and/or the pharmacy. The program processor may determine the location from other source devices or may maintain a directory of the location, as may be applicable. From the location, the program processor determines 310 longitude and latitude of the location. The program processor may determine the longitude and latitude from another source device or may maintain a record of the location, as may be applicable.

The program processor generates 312 an updated token with rules for the location. The rules for the location cause a user device having a digital wallet with the updated token to display a location-based message if and when the user device passes to within a threshold distance of the location.

Figure 4:
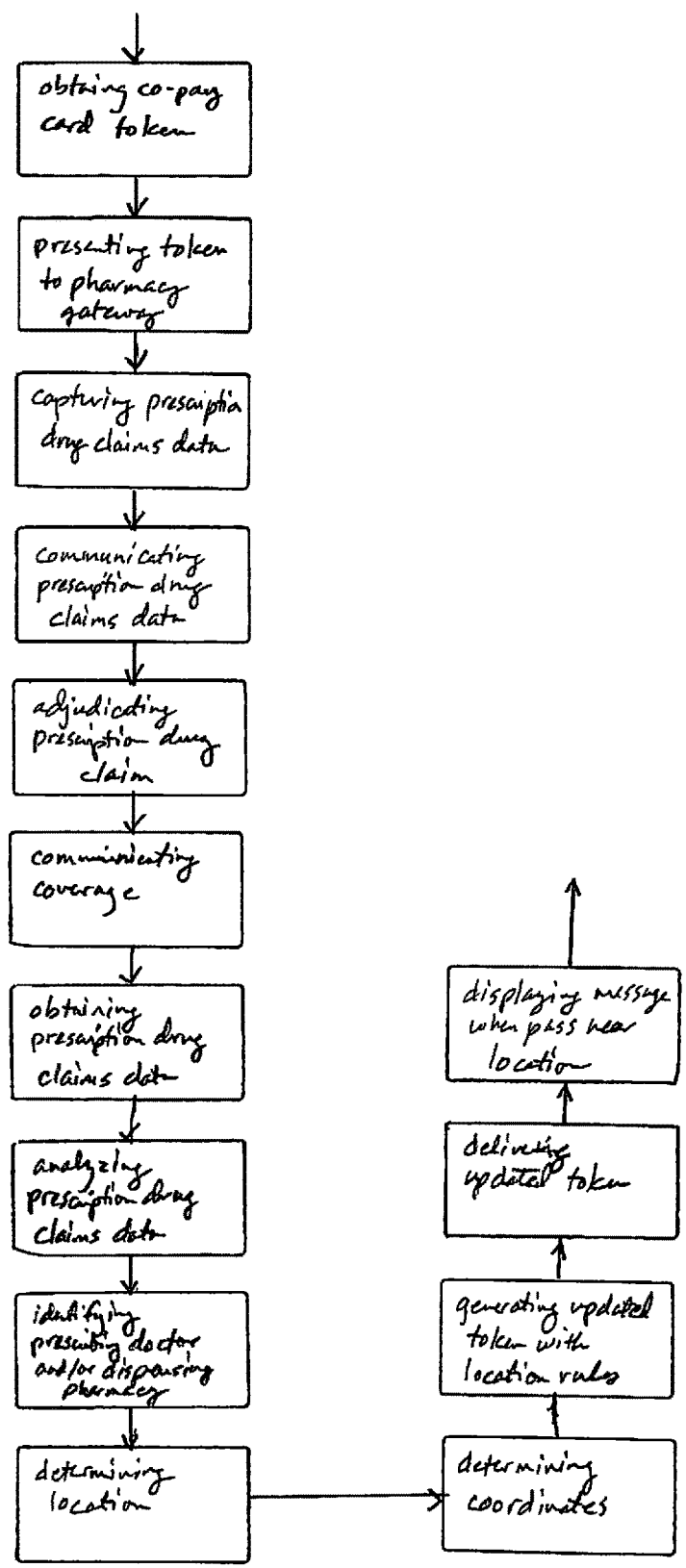
FIG. 4 illustrates a method of operations of a system for delivering messaging to a user device via digital wallet tokens with rules for display of messaging based on location, according to certain embodiments of the invention.

Referring to FIG. 4, a method 400 of operations of a system includes obtaining 402 a co-pay card token by a digital wallet of a user device. The user device presents 404 the token at point of purchase using the digital wallet to a pharmacy gateway. The pharmacy gateway captures 406 prescription drug claims data and communicates 408 the data to a claims processor. The claims processor adjudicates 410 the prescription drug claim of the prescription drug claims data and communicates 412 with the pharmacy gateway to account for any coverage benefit and/or co-pay coverage in connection with purchase of the prescription drug of the token.

A program processor obtains 414 the prescription drug claims data from the claims processor. The program processor analyzes 416 the prescription drug claims data. From the analyzing 416, the program processor identifies 418 a prescribing doctor and/or dispensing pharmacy associated with the prescription drug claims data. The program processor determines 420 a location of the prescribing doctor and/or the dispensing pharmacy. Determining 420 the location may be by look-up in a directory accessible from an online source or otherwise.

The program processor determines 422 longitude and latitude coordinates for the location of the prescribing doctor and/or the dispensing pharmacy. Determining 422 the longitude and latitude coordinates may be by look-up in a directory accessible from an online source or otherwise. Based on the longitude and latitude coordinates of determining 422, the program processor generates 424 an updated token for the digital wallet of the user device. The updated token includes rules for display of a message in the user device if and when the user device passes to within a threshold distance of the location of the prescribing doctor and/or the dispensing pharmacy.

The updated token is delivered 426 to the digital wallet of the user device. If and when the user device passes to within the threshold distance as per the rules of the updated token, the user device displays 428 a message in the user device.

Various alternatives and additions are possible in the foregoing embodiments. In certain alternatives, the claims processor is a computer or computers operated by a health insurance provider, pharmacy benefits provider, government program, third party payer system, drug manufacturers, other vendors and/or business associates of healthcare service providers, government and/or non-government entities providing financial and/or administrative services, or other vehicle for adjudication of prescription drug claims. In other alternatives, the claims processor is another node of the communications network, such as a switch or other transceiver of the network, that receives and transmits claims data. The particular claims data that is received by the program processor may be widely varied. The program processor accordingly is programmed for the variety of the claims data.

The program processor may, in certain alternatives, be operated by a discount or other award program provider. The discount or other award program may include communication of discount coupons or other awards. In other alternatives, the program processor may operate a health management program, alone or in conjunction with other program, such as a discount or award program. The health management program may itself include discount or award coupons and other advantages to program enrollees for adherence to health regimen or otherwise.

In other alternatives, the program processor and claims processor may be unitized or include a distributed computing environment. Applicable communications between pharmacy gateway, claims processor, program processor, and/or user device may be over same or disparate communications networks, which may be selected from wide variety of various channels or links, including wired and wireless links. For example, the communications between the pharmacy gateway and the claims processor, as well as between the claims processor and the program processor, may be by dedicated, secure network, or other secure channels. Communications between the program processor and the user device may be secured and include public or private networks, including, for example, wireless cellular or other wireless channels.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention.

Benefits, other advantages, and solutions to problems have been described above with regard to specific embodiments. However, the benefits, advantages, solutions to problems and device(s), connection(s) and element(s) that may cause any benefit, advantage, or solution to occur or become more pronounced are not to be construed as a critical, required, or essential feature or element of any or all the claims. As used herein, the terms "comprises, "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system for generation of an updated digital wallet token, comprising:
    a digital wallet stored on non-transitory, computer-readable memory of a user device, the digital wallet configured to store a digital wallet token, the user device including a location sensor;
    a pharmacy gateway comprising a first network device including at least one processor and configured to receive prescription drug claims data upon a request of fulfillment of a prescription;
    a claims processor comprising a second network device and communicatively connected to the pharmacy gateway via a network, wherein the claims processor obtains the prescription drug claims data from the pharmacy gateway and is configured to adjudicate the prescription drug claims data to determine benefit coverage corresponding to the purchase of the prescription drug; and a program processor comprising a third network device and communicatively connected to the user device via the network, wherein the program processor is configured to:

obtain the prescription drug claims data from the pharmacy gateway via the network, wherein the prescription drug claims data includes details of a transaction for purchase of a prescription drug and an identity of at least one of a prescribing doctor or a dispensing pharmacy, parse the prescription drug claims data to identify an entity being one of the prescribing doctor or the dispensing pharmacy as included in the details of the transaction, determine a location of the entity by performing a looking up for location information of the prescribing doctor or the dispensing pharmacy in a database via the network, generate the updated digital wallet token, wherein the updated digital wallet token includes one or more rules configured to cause display of a message on a display screen of the user device when the location sensor detects that the user device passed to within a threshold distance of the location of the entity, wherein the message corresponds to the prescription drug purchase at least due to the location of the entity triggering display of the message being derived from the prescription drug claims data, and transmit the updated digital wallet token to the digital wallet of the user device, wherein, in response to detection by the location sensor of the user device that the user device is within a threshold distance of the location of the entity, executing, by a processor of the user device, the one or more rules of the updated digital wallet token thereby causing rendering of the message on the display screen.

2. The system of claim 1 wherein the pharmacy gateway determines the prescription drug claims data for the purchase of the prescription drug based on the digital wallet token of the user device.

3. The system of claim 1, wherein determining the location of the entity includes determining longitude and latitude coordinates of the entity.

4. The system of claim 1, wherein the message rendered on the display screen of the user device includes one or more of a coupon or an advertisement.

5. A method for generating of an updated digital wallet token, comprising:

obtaining, by a pharmacy gateway, prescription drug claims data upon a request of fulfillment of a prescription, wherein the pharmacy gateway comprises a first network device including at least one processor;

obtaining, by a claims processor, the prescription drug claims data from the pharmacy gateway and is configured to adjudicate the prescription drug claims data to determine benefit coverage corresponding to the purchase of the prescription drug, wherein the claims processor comprises a second network device and is communicatively connected to the pharmacy gateway via a network;

obtaining, by a program processor, the prescription drug claims data from a pharmacy gateway via the network, wherein the prescription drug claims data includes details of a transaction for purchase of a prescription drug and an identity of at least one of a prescribing doctor or a dispensing pharmacy, wherein the program processor comprises a third network device, and wherein a first digital wallet is stored in a digital wallet that is stored on non-transitory, computer-readable memory of a user device, the user device including a location sensor;

parsing, by the program processor, the prescription drug claims data to identify a prescribing doctor or a dispensing pharmacy associated with the prescription drug claims data as included in the details of the transaction;

determining, by the program processor, a location of the prescribing doctor or the dispensing pharmacy by performing a looking up for location information of the prescribing doctor or the dispensing pharmacy in a database via the network;

generating an updated digital wallet, wherein the updated digital wallet token includes one or more rules configured to cause display of a message on a display screen of the user device when the location sensor detects that the user device passed to within a threshold distance of the location of the entity, wherein the message corresponds to the prescription drug purchase at least due to the location of the entity triggering display of the message being derived from the prescription drug claims data;

transmitting the updated digital wallet token to the digital wallet of the user device; and in response to detection by the location sensor of the user device that the user device is within a threshold distance of the location of the entity, executing, by a processor of the user device, the one or more rules of the updated digital wallet token thereby causing rendering of the message on the display screen.

6. The method of claim 5, further comprising:

determining, by the pharmacy gateway, the prescription drug claims data for the purchase of the prescription drug based on the digital wallet token of the user device, wherein the pharmacy gateway is communicatively connected to a claims processor.

7. The method of claim 6, further comprising:

obtaining, by the claims processor, the prescription drug claims data and adjudicating the prescription drug claims data to determine benefit coverage corresponding to the purchase of the prescription drug.

8. The method of claim 5, wherein determining the location of the entity includes determining longitude and latitude coordinates of the entity.

9. The method of claim 5, wherein the message rendered on the display screen of the user device includes one or more of a coupon or an advertisement.

* * * * *